United States Patent [19]

Tronzo

[11] Patent Number: 4,940,467
[45] Date of Patent: Jul. 10, 1990

[54] VARIABLE LENGTH FIXATION DEVICE

[76] Inventor: Raymond G. Tronzo, 255 Clarke Ave., Palm Beach, Fla. 33480

[21] Appl. No.: 443,824

[22] Filed: Nov. 30, 1989

Related U.S. Application Data

[63] Continuation of Ser. No. 151,947, Feb. 3, 1988, abandoned.

[51] Int. Cl.⁵ .............................................. A61B 17/58
[52] U.S. Cl. ....................................... 606/66; 606/65; 606/73
[58] Field of Search ................................... 606/65–68, 606/73

[56] References Cited

U.S. PATENT DOCUMENTS

| | | | |
|---|---|---|---|
| 2,397,545 | 4/1946 | Hardinge | 606/65 |
| 2,511,051 | 6/1950 | Dzus | 128/92 YF |
| 2,612,159 | 9/1952 | Collison | 606/67 |
| 2,682,265 | 6/1954 | Collison | 128/92 YK |
| 2,702,543 | 2/1955 | Pugh et al. | 606/67 |
| 3,051,169 | 8/1962 | Grath | 128/92 YV |
| 3,990,438 | 11/1976 | Pritchard | 606/73 |
| 4,103,683 | 8/1978 | Neufeld | 606/67 |
| 4,172,452 | 10/1979 | Forte et al. | 128/92 YZ |
| 4,341,206 | 7/1982 | Perrett et al. | 606/80 |
| 4,381,770 | 5/1983 | Neufeld | 606/67 |
| 4,438,762 | 3/1984 | Kyle | 606/65 |
| 4,441,492 | 4/1984 | Rydell et al. | 128/92 YK |
| 4,450,835 | 5/1984 | Asnis et al. | 606/73 |
| 4,463,753 | 8/1984 | Gustilo | 128/92 YV |
| 4,530,355 | 7/1985 | Griggs | 606/105 |
| 4,628,923 | 12/1986 | Medoff | 128/92 YK X |
| 4,640,271 | 2/1987 | Lower | 128/92 YF |
| 4,641,640 | 2/1987 | Griggs | 606/66 |
| 4,653,489 | 3/1987 | Tronzo | 606/65 |
| 4,776,329 | 10/1988 | Treharne | 128/92 YV |

FOREIGN PATENT DOCUMENTS

1007659 3/1983 U.S.S.R. .......................... 128/92 YZ

OTHER PUBLICATIONS

Asnis Guided Screw System Brochure.

*Primary Examiner*—Robert A. Hafer
*Assistant Examiner*—Kevin G. Rooney, Jr.
*Attorney, Agent, or Firm*—Eugene Chovanes

[57] ABSTRACT

A variable length fixation device for insertion into a hole formed in two or more bone fragments has a barrel portion and a fastener element. The barrel portion is secured to an inside surface of the hole in a proximal one of the bone fragments. The fastener element is telescopically mounted to the barrel portion and is extendable into a distal one of the bone fragments. The assembly prevents lateral movements of the distal fragment, relative to the proximal fragment, while allowing axial relative movements (i.e., linear movements along the longitudinal axis of the fastener element) to occur. In a preferred embodiment, the fastener element is a cannulated bone screw having a hex-shaped cross-section on one end which is telescopically received into a hex-shaped interior of the hollow barrel portion. The two components are preferably permanently joined to form a one-piece assembly having a variable overall length. The fixation device of the present invention is substantially insertable in its entirety into the hole which extends across the fracture site, and may be installed with a minimal amount of trauma and damage to surrounding bone and soft tissues.

6 Claims, 2 Drawing Sheets

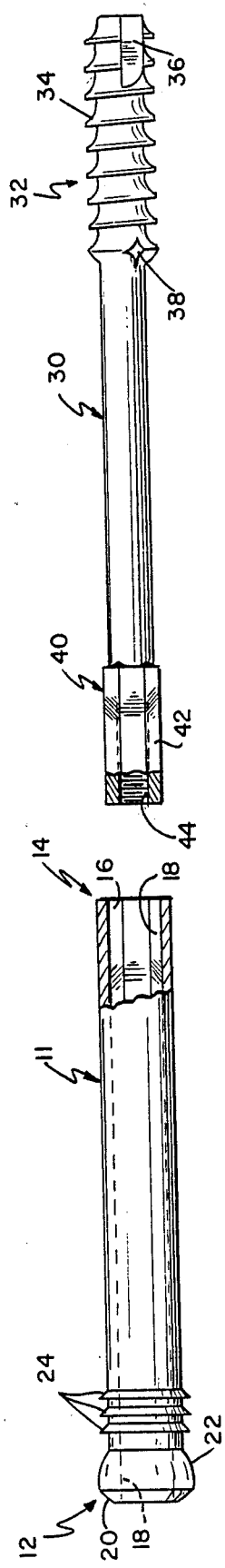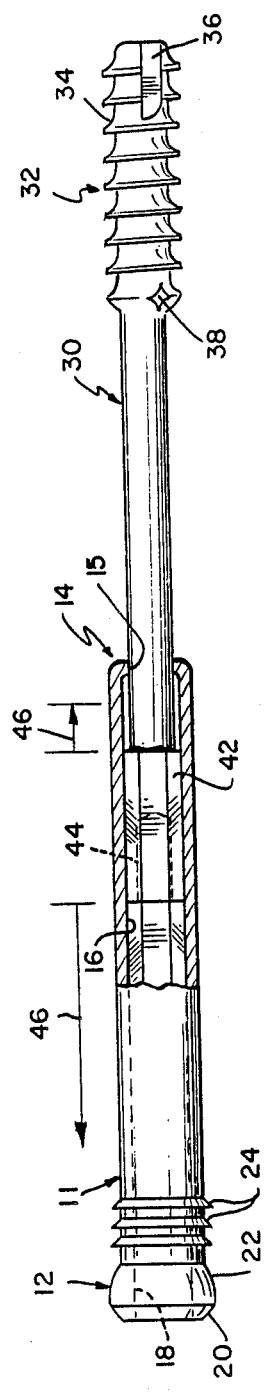
FIG. 1
FIG. 2
FIG. 3

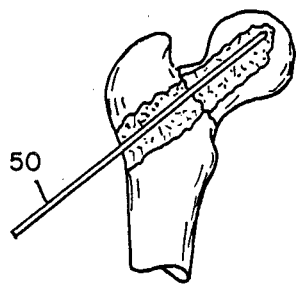
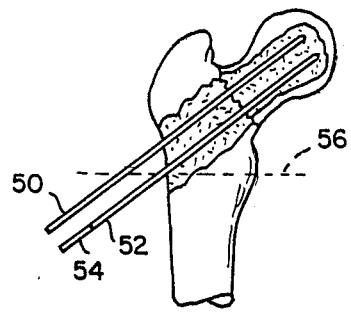
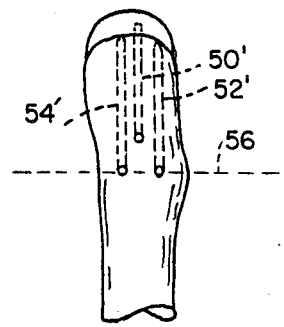
FIG. 4   FIG. 5   FIG. 6
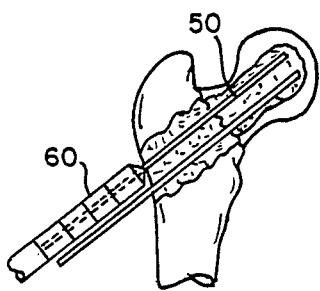
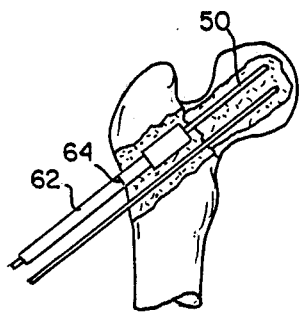
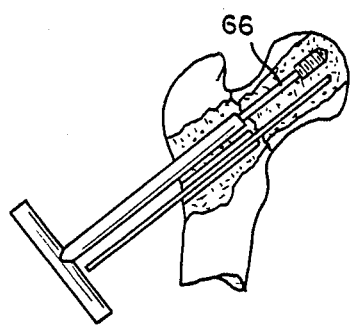
FIG. 7   FIG. 8   FIG. 9
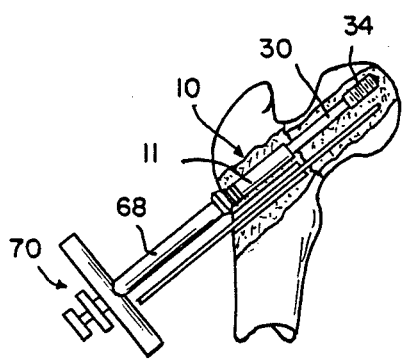
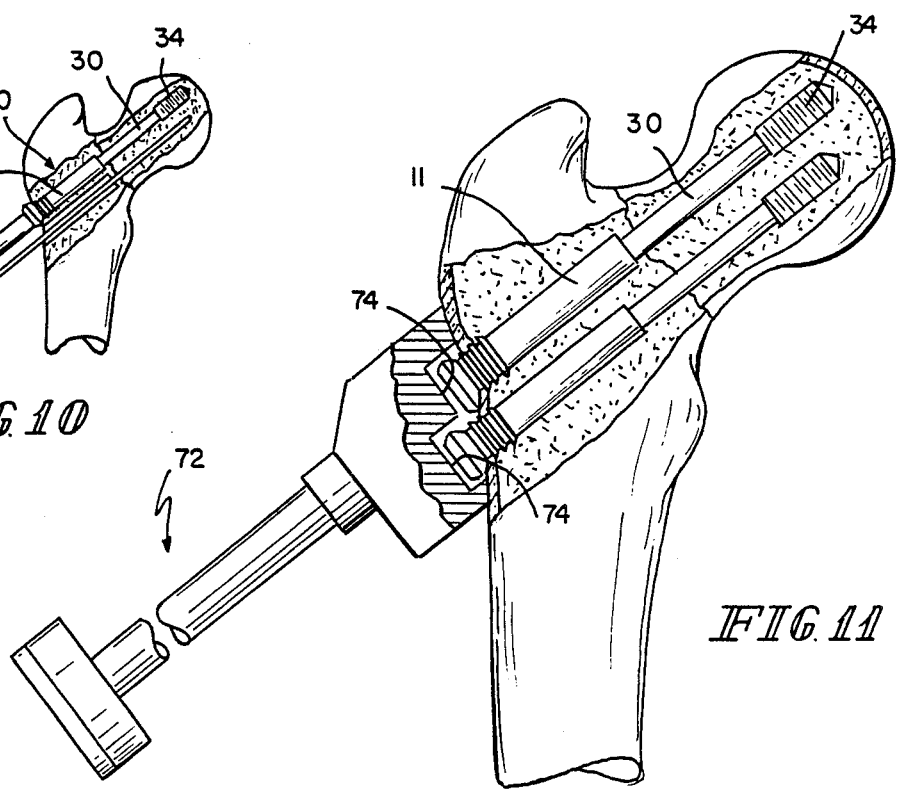
FIG. 10   FIG. 11

VARIABLE LENGTH FIXATION DEVICE

This application is a continuation of application Ser. No. 151,947, filed Feb. 3, 1988, now abandoned.

BACKGROUND AND SUMMARY OF THE INVENTION

This invention relates generally to orthopedic fixation devices and, more particularly, to a variable length fixation device which is especially well-suited for fixation of fractures of the femoral neck, tibial plateau and pelvis.

Fractures of the type which commonly occur in the femoral neck, tibial plateau and pelvis require internal fixation for proper and timely healing. Such fixation is normally accomplished with nails or lag screws which hold the fractured pieces of bone together along the fracture site until healing is complete.

One known technique for fixation of fractures of the above types is the so-called Asnis Guided Screw System presently marketed by Howmedica, Inc., of N.Y., N.Y., and partially described in U.S. Pat. Nos. 4,383,527 and 4,450,835. The Asnis system utilizes one or more rigid lag screws which are installed across a fracture site over guide pins to rigidly secure the bone fragments in close proximity to one another. In treating a fracture of the femoral neck, for example, three or four screws are inserted through the lateral cortex of the femur, and extend across the fracture site and into the subchondral region of the femoral head. Each screw must be carefully selected for the exact size because they are "fixed length screws."

The rigid screws of the Asnis system may provide relatively good initial fixation of the fracture. However, during the post-operative period, resorption of bone on either side of the fracture line may occur. In this event, a fracture which has been fixed with rigid screws may no longer be firmly compressed or impacted along the fracture line. The rigid screws assume the primary load bearing function, and physiological compression which might otherwise occur at the fracture site is prevented. Alternatively, the screws may "slide" in the holes drilled in the femur as resorption occurs, and the heads of the screws will be forced outwardly away from the femur and into the surrounding soft tissues, i.e., the heads become "extruded." Under these conditions, an extended period may be required for complete and proper healing of the fracture, or the extrusion of the screws may result in loss of the fracture fixation and/or subsequent loss of the fracture reduction which may result in the fracture failing to unite which is otherwise known as a non-union.

Use of the Asnis system requires proper selection of screw size (i.e., length) to fit a particular fracture and bone size. An inventory of twenty screw sizes with lengths ranging from 35 mm to 130 mm in 5 mm increments is recommended.

Other known devices for fixation of fractures of the femoral neck are illustrated and described in U.S. Pat. Nos. 2,612,159; 2,702,543 and 4,438,762. These devices typically depend on a side plate (often referred to as a trochanteric plate in the above-referenced patents) which has a shank portion and a tubular guide sleeve which form an angle with each other of approximately 135 degrees. The shank portion is provided with a number of holes and is positioned along the lateral cortex of the femur below the area of the fracture. A plurality of bone screws extend through the holes in the shank and into the shaft of the femur to hold the plate in position. The tubular guide sleeve extends into a hole which has been drilled or reamed into the femur, and which extends along the center line of the femoral neck. A single lag screw or nail extends through the guide sleeve, across the fracture site and into the femoral head. The nail or screw is free to move telescopically within the guide sleeve so that contact between the bone fragments is maintained, notwithstanding the occurrence of resorption at the fracture site. The tubular guide sleeve of the plate, which is firmly attached to the shank of the femur, provides lateral support for the nail or screw and, at least in some cases, is designed to prevent relative rotation between the bone fragment attached to the nail or screw and the shank of the femur.

Use of a fixation device which incorporates a side plate requires the insertion of additional holes and screws into the shaft of the femur, which may already be weakened by the original injury, or by osteopathic disease. The installation and removal of these devices require relatively large incisions and a relatively complex surgical procedure. The recovery period during which the patient must be at least partially immobilized is increased, along with the probabilities of occurrence of infections and other complications.

An object of the present invention is to provide a fixation device which is simple to install and to remove, and which may be installed and removed with a minimal amount of trauma and damage to surrounding tissues.

Another object of the present invention is to provide a fixation device having a variable length which may be versatilely used in a number of fracture types and situations. A major practical advantage is one of cost since two of these screws can greatly reduce the number of device sizes which must be maintained in inventory.

Yet another object of the present invention is to provide a fixation device which avoids or minimizes other problems associated with prior art devices, while offering advantageous features to both surgeon and patient in the treatment of many types of fractures.

These and other objects of the invention are attained in a variable length fixation device for insertion into an opening formed in one or more bone fragments which comprises a barrel portion, means for securing the barrel portion to an interior surface of the opening in the bone fragments, and a fastener element. The fastener element is telescopically mounted to the barrel portion and extends into a distal one of the bone fragments for preventing lateral movements of the distal fragment relative to the barrel portion and a proximal one of the fragments. The opening in the bone fragments extends along a line which is substantially transverse to a plane of fracture between the fragments, and the telescopically mounted fastener means allows axial relative movements (i.e., movements parallel to the longitudinal axis of the fastener) of the fragments along the transverse line of the opening.

In a preferred embodiment, the means for securing the barrel portion to the interior surface of the opening comprises a plurality of locking rings formed on an outer surface of the barrel portion. The locking rings interact with a surface of the opening in the proximal bone fragment to prevent axial movements (i.e., migration into or out of the opening) of the barrel portion subsequent to insertion of the device. The fastener element preferably comprises a screw portion having a plurality of threads on a first end thereof for fastening to the distal bone fragment, and having means on a second end thereof for slidably mounting the screw portion to the barrel portion. In an especially preferred embodiment, the screw portion has a hexagonally-shaped cross-section and outer surface. In this embodiment, the barrel portion is hollow and has a hexagonally-shaped inner surface. The hexagonally-shaped outer surface of the screw portion is slidably mounted within the hollow barrel portion in an adjacent and mating relationship to the hexagonally-shaped inner surface, such that the screw portion is rotationally fixed relative to the barrel portion.

A preferred embodiment of the present invention includes means for detachably connecting a wrench to the barrel portion to allow the barrel portion to be rotated which automatically advances the screw portion into the distal fragment. This means is preferably a hexagonally-shaped recess in a proximal end of the barrel portion. In a preferred embodiment of the invention, the barrel portion and the fastener element are cannulated (i.e., hollow) and are adapted for insertion over a guide pin positioned along the transverse line of the opening. The barrel portion and fastener element are preferably permanently assembled to form a unitary fixation device.

An especially preferred embodiment of the invention is termed a Variable Length Compression (VLC ™) bone screw assembly which comprises a barrel portion and a screw portion. The barrel portion is provided with means for securing the barrel portion to an interior surface of the opening in the proximal fragment to prevent axial movements of the barrel portion subsequent to insertion. The screw portion has a first end which is provided with means for fastening the screw portion to the distal bone fragment, and a second end which is mounted to the barrel portion. The screw portion is axially movable, but rotationally fixed, relative to the barrel portion and is preferably cannulated (i.e., hollow). In this preferred embodiment, the barrel portion is hollow and the second end of the screw portion is telescopically mounted within the barrel portion. The second end of the screw portion has a hexagonal cross-section, and an internal shape of the hollow barrel portion has a matching hexagonal cross-section such that, when the two hexagonal cross-sections are placed together in mating relationship with each other, relative rotation of the barrel portion and screw portion is prevented. The cannulated screw portion is further provided with threads on at least a portion of an internal surface to provide a means for connecting the screw portion to a compression tool. In the preferred embodiment of the invention, the means for fastening the first end of the screw portion to the distal bone fragment comprise a plurality of cancellous screw threads. Self-cutting flutes are provided on either end of the threads for easing insertion into and extraction from the distal bone fragment. The barrel portion and the screw portion are preferably permanently assembled by a swaging technique to form the complete bone screw assembly.

A preferred method of installing the bone screw assembly of the present invention includes a first step of placing a guide pin across the fracture site to define the desired location for placement of the bone screw assembly. A cannulated reamer is used to widen at least an outer portion of the hole to accommodate the barrel of the bone screw assembly. If desired or required, the remaining portion of the hole may be tapped to reduce the effort required for insertion of the screw portion into relatively dense bone tissue. After the hole has been reamed and, in some cases, tapped, the bone screw assembly is inserted into the hole, and a tool is used to turn the barrel portion, causing the barrel portion to twist the screw portion into the bone fragment. The screw portion is advanced under fluoroscopic control until the desired level of penetration has been achieved. After the required number of bone screw assemblies have been installed, the fracture may be compressed or impacted, as desired.

The design of the bone screw assembly of the present invention permits physiological compression at the fracture site during the post-operative period, notwithstanding the possible occurrence of resorption of bone tissue along the fracture. Accordingly, firm fixation is dynamically maintained throughout the period of fracture healing. Other advantages include ease of installation and removal, reduced trauma to surrounding bone and soft tissues, greater versatility resulting from the variable length feature, and reduced cost for inventory requirements.

Other objects, advantages and novel features of the present invention will become apparent from the following detailed description of the invention, when considered in conjunction with the accompanying drawings.

BRIEF DESCRIPTION OF THE DRAWINGS

FIG. 1 shows a side view of the barrel portion of a preferred embodiment of the variable length fixation device of the present invention.

FIG. 2 shows a side view of the screw portion of a preferred embodiment of the variable length fixation device of the present invention.

FIG. 3 shows a side view of a preferred embodiment of the variable length fixation device of the present invention.

FIGS. 4–11 illustrate the steps of a preferred method of using the preferred embodiment of FIG. 3 in treating a fracture of the femoral neck.

DETAILED DESCRIPTION OF THE DRAWINGS

A preferred embodiment of the present invention is shown in FIGS. 1, 2 and 3. This preferred embodiment is designated a Variable Length Compression Screw, or a VLC ™ Screw. The complete bone screw assembly (10) is shown in FIG. 3. Bone screw assembly 10 comprises two main component parts which are separately illustrated in FIGS. 1 and 2, and which are discussed in detail below.

FIG. 1 shows a side view of barrel portion 11 of the present invention. Barrel portion 11 is a generally elongate hollow structure having a head portion 12 on a first end thereof. The opposite end 14 of barrel portion 11 is open to receive the screw portion (30 in FIG. 2) of bone screw assembly 10, as described in detail below. Inner surface 16 of barrel portion 11 is hex-shaped throughout at least a portion (and preferably the entire length) of barrel portion 11. Hex-shaped interior surface 16 extends all the way through head portion 12 or, alternatively, a hex-shaped recess 18 is provided in the end of head portion 12 to receive a detachable tool or wrench which is used to rotate barrel portion 11 and, in the preferred embodiment, the rest of bone assembly 10. Outer surfaces 20 and 22 of head portion 12 are spherical in shape, such that the overall shape of head portion 12 is that which would result from the intersection of portions of two spherical bodies. As illustrated in FIG. 1, the overall diameter of the widest point of head portion 12 (i.e., the intersection of spherical surfaces 20 and 22) is only slightly larger than the diameter of the remaining portions of barrel portion 11. Barrel portion 11 is further provided with three equally spaced locking rings 24 immediately adjacent head portion 12. As will be explained below, locking rings 24 are intended to prevent outward migration of barrel portion 11 after placement of bone assembly 10 within a hole formed in a bone.

FIG. 2 shows screw portion 30 of bone screw assembly 10. Screw portion 30 has a first end 32 which is provided with a plurality of threads 34 for fastening screw portion 30 to bone tissue. A plurality of cutting flutes 36 are provided on the outer end of threads 34 to ease the process of inserting or threading screw portion 30 into bone tissue. Cutting flutes 38 are also provided on the opposite end of threads 34 to ease the process of extracting bone screw assembly 10 after healing of the fracture is complete.

A second end 40 of screw portion 30 preferably has a hexagonally-shaped outer surface 42 which extends axially along at least a portion of the outer surface of screw portion 30. Hex-shaped outer surface 42 is intended to mate with hex-shaped inner surface 16 of barrel portion 11, such that when the two portions 11 and 30 are joined, relative axial rotation between the two is prevented. The mating relationship between surfaces 16 and 42 is such that axial relative movement between portions 11 and 30 is uninhibited. Screw portion 30 is cannulated (i.e., hollow) and a portion of the inner surface of screw portion 30 is provided with threads 44 for purposes of compressing a fracture, as will be described in additional detail below.

FIG. 3 shows a side view of bone screw assembly 10 after barrel portion 11 and screw portion 30 have been joined. Barrel portion 11 and screw portion 30 are preferably permanently joined by swaging end portion 14 of barrel portion 11 to form an inwardly extending lip 15 around the circumference of end portion 14, subsequent to insertion of screw portion 30 within barrel portion 11, to prevent subsequent disassembly. As discussed, mating hex-shaped surfaces 16 and 42 prevent relative rotational movement between portions 11 and 30. However, as illustrated by arrow 46, relative axial movements between portions 11 and 30 are uninhibited.

FIGS. 4-11 illustrate a preferred method of using bone screw assembly 10. As previously noted, bone screw assembly 10 is especially well-suited for fixation of fractures occurring in the femoral neck, the tibial plateau, and pelvis. For purposes of illustration, FIGS. 4-11 describe the use of bone screw assembly 10 for fixation of a fracture of the femoral neck.

After the fracture has been reduced and the femur exposed, guide pin 50 is introduced through the lateral cortex of the femur. Guide pin 50 will be used to ensure proper lateral placement of bone screw assembly 10. Two additional guide pins 52 and 54 are placed below guide pin 50 in spaced apart relation and in parallel to guide pin 50 to form a preferred triangular configuration. The triangular configuration of holes 50', 52' and 54', each of which accept a corresponding guide pin, is shown in FIG. 6. Each pin extends through the lateral cortex and across the fracture site into an acceptable position and depth in the femoral head. All guide pins and screw assemblies are preferable kept at or above the level of the lesser trochanter (indicated by dotted line 56 in FIGS. 5 and 6) to prevent the possible creation of stress risers which might jeopardize the integrity of the femoral shaft at the subtrochanteric level.

With reference to FIG. 7, a direct measurement gauge 60 is used to determine the correct VLC ™ screw size. An advantage to the present invention is that the variable length feature of bone screw assembly 10 allows for a drastic reduction in the required number of screw sizes. At present, two screw sizes are contemplated. The first will range from 59 mm to 76 mm (2-5/16" to 3"), and the second will range from 76 mm to 110 mm (3" to 4-5/16").

Following measurement to determine proper screw size, a cannulated reamer 62 is placed over the guide pins to form three parallel holes in the proximal bone fragment (i.e., the femur) which will receive barrel portion 11 of bone screw assembly 10 (see FIG. 8). Each hole is drilled along a line which extends generally transversely to a plane which extends, in a generally coplanar relationship, across the fracture site in the femoral neck. A groove 64 on the body of reamer 62 indicates proper depth for reaming. Reaming beyond the depth indicated by groove 64 may cause unnecessary bone loss and prevent proper screw fixation. As illustrated in FIG. 9, a cannulated bone tap 66 may be used over the guide pins when hard, dense bone is encountered in the femoral head. Alternatively, screw portion 30 may be threaded directly into the distal bone fragment (i.e., the femoral head) without tapping or reaming this portion in advance.

After the guide pins have been placed and measured, and after the holes have been reamed and (if desired) tapped, bone screw assembly 10 is inserted into each of the holes (see FIG. 10). A T-shaped hex wrench 68 is used to rotate barrel portion 11 and, consequently, screw portion 30 into position over the guide pin. When wrench 68 is pushed and rotated in a clockwise direction, threads 34 of screw portion 30 will engage the bone tissue and screw portion 30 will telescopically advance out of barrel portion 11 along the guide pin. Screw portion 30 is advanced under fluoroscopic control to the subchondral level of the joint, or until desired placement is achieved. After a screw assembly has been placed in each of the three holes, locking rings 24 on the barrel of each assembly are seated into the lateral cortex by tapping on the handle of wrench 68 (see FIG. 10) which drives the rings into the cortex. The rings serve to prevent the barrel from backing out of the upper femoral shaft.

After the bone screw assemblies are in place, the fracture may be compressed or impacted, as preferred. For fractures of the pelvis, tibial plateau and femoral neck in younger patients, where osteopenia infrequently occurs, a compression tool 70 may be used to compress the fracture. A compression rod extends through the hollow barrel portion 11 of the screw assembly and is threaded into internal threads 44 of screw portion 30. The compression rod is then placed in tension, while barrel portion 11 is held in place, to draw the bone fragments together by drawing screw portion 30 into barrel portion 11 to firmly compress the fracture. This is especially valuable for bringing together the two major fragments of bone in femoral neck fractures, tibial plateau fractures, and pelvic fractures. Alternatively, an impaction tool (72 in FIG. 11) may be placed against the femur in the area immediately adjacent the bone screw assemblies, and firm impaction of the fracture can be achieved by tapping on the end of the impaction tool. Impaction tool 72 preferably has recessed holes 74 which are placed over the heads of the bone screw assemblies to allow the impaction forces to be equally distributed on the lateral cortex of the femur around the screws.

Although the present invention has been described and illustrated by reference to a particularly preferred embodiment (i.e., the VLC™ bone screw assembly), other types of fixation devices may advantageously incorporate the features of the present invention. In its broadest sense, the present invention is intended to encompass such devices (for example, a variable length nail). Furthermore, although the fixation device of the present invention is shown and discussed with reference to a particular type of fracture, and although the specific embodiment shown is particularly well-suited for treating certain types of fractures, use of the invention is not limited to these applications.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A screw for fixing proximal and distal fragments in a bone fracture, comprising
   (A) a first and second element that
      (1) are non-separably interconnected,
      (2) each have a longitudinal axis in line with the other,
      (3) longitudinally telescope with each other, and
      (4) have means for rotationally fixing the elements to each other;
   (B) the first element having
      (1) a first shank portion, and
      (2) screw threads at one end of the first shank portion integral therewith for engaging the distal fragment;
   (C) the second element having
      (1) a second shank portion in the form of a sleeve, free of threads on its outer surface for engaging the proximal fragment that longitudinally, slidably fits over the first shank portion of the first element, and
      (2) a head at an end of the second shank portion remote from the screw threads on the first shank portion for receiving means for turning the screw.

2. A screw of claim 1 having means for retaining the second element in the proximal fragment.

3. The screw of claim 2 wherein the means for retaining the second element in the proximal fragment comprise a plurality of locking rings formed on the outer surface of the second element.

4. A screw of claim 1 wherein the means for rotationally fixing the elements to each other comprise a hexagonally-shaped outer surface on the first shank portion, and a hexagonally-shaped inner surface in the second shank portion.

5. A screw of claim 1 wherein the head of the second element has a hexagonally-shaped recess to receive wrench means for turning the screw.

6. A screw of claim 1 wherein the first and second element are hollow and are adapted for insertion over a guide pin positioned in the proximal and distal fragments.

* * * * *